United States Patent
Kaltschmidt et al.

(10) Patent No.: US 10,546,398 B2
(45) Date of Patent: Jan. 28, 2020

(54) DEVICE AND METHOD FOR FINE ADJUSTMENT OF THE RECONSTRUCTION PLANE OF A DIGITAL COMBINATION IMAGE

(71) Applicant: SIEMENS HEALTHCARE GMBH, Erlangen (DE)

(72) Inventors: Rainer Kaltschmidt, Eckental Oberschoellenbach (DE); Christian Schmidgunst, Erlangen (DE); Thomas Schmitt, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/998,776

(22) Filed: Aug. 16, 2018

(65) Prior Publication Data

US 2019/0057524 A1  Feb. 21, 2019

(30) Foreign Application Priority Data

Aug. 16, 2017  (DE) ............... 10 2017 214 246

(51) Int. Cl.
*G06T 11/00*  (2006.01)
*A61B 6/00*  (2006.01)

(52) U.S. Cl.
CPC .......... *G06T 11/005* (2013.01); *A61B 6/4452* (2013.01); *A61B 6/5241* (2013.01); *G06T 2200/24* (2013.01)

(58) Field of Classification Search
None
See application file for complete search history.

(56) References Cited

U.S. PATENT DOCUMENTS

| | | | |
|---|---|---|---|
| 7,218,766 B2 | 5/2007 | Eberhard et al. | |
| 7,421,057 B2 | 9/2008 | Watanabe | |
| 9,109,998 B2 | 8/2015 | Nathaniel et al. | |
| 9,858,663 B2 | 1/2018 | Penney et al. | |
| 9,968,311 B2 | 5/2018 | Tagawa et al. | |
| 2007/0171524 A1* | 7/2007 | Steinthal | G02B 7/06 359/466 |
| 2011/0188726 A1 | 8/2011 | Nathaniel et al. | |

(Continued)

FOREIGN PATENT DOCUMENTS

| | | |
|---|---|---|
| CN | 1973771 A | 6/2007 |
| CN | 102124320 A | 7/2011 |

(Continued)

*Primary Examiner* — Delomia L Gilliard
(74) *Attorney, Agent, or Firm* — Laurence Greenberg; Werner Stemer; Ralph Locher

(57) ABSTRACT

A method and a device for fine adjustment of the reconstruction plane of a digital combination image from individual images of a digital radiology system. The device includes an interface for providing individual images of an object. The individual images have overlapping regions with one another. A distance controller, with which the distance A of the individual images can be changed. A processing unit calculates a current combination image from the individual images. The individual images are each shifted by the distance A in relation to one another. A display unit displays the current combination image from the individual images. There is also described an image evaluation system and/or digital radiology system which includes the device.

19 Claims, 4 Drawing Sheets

(56) References Cited

U.S. PATENT DOCUMENTS

| | | |
|---|---|---|
| 2013/0315372 A1 | 11/2013 | Behiels |
| 2014/0126688 A1* | 5/2014 | Flohr .................. G01N 23/046 378/19 |
| 2015/0297311 A1* | 10/2015 | Tesar .................... G02B 21/16 600/411 |
| 2016/0042537 A1 | 2/2016 | Ng et al. |
| 2017/0224298 A1 | 8/2017 | Hannemann et al. |
| 2018/0303574 A1* | 10/2018 | Ramirez Luna ....... A61B 90/37 |
| 2018/0343431 A1* | 11/2018 | Veldandi .............. H04N 5/2226 |

FOREIGN PATENT DOCUMENTS

| | | |
|---|---|---|
| CN | 103429157 A | 12/2013 |
| CN | 105997113 A | 10/2016 |
| CN | 106572829 A | 4/2017 |

\* cited by examiner

DEVICE AND METHOD FOR FINE ADJUSTMENT OF THE RECONSTRUCTION PLANE OF A DIGITAL COMBINATION IMAGE

CROSS-REFERENCE TO RELATED APPLICATION

This application claims the priority, under 35 U.S.C. § 119, of German patent application DE 10 2017 214 246.4, filed Aug. 16, 2017; the prior application is herewith incorporated by reference in its entirety.

BACKGROUND OF THE INVENTION

Field of the Invention

The invention relates to a device and also to a method for fine adjustment of the reconstruction plane of a digital combination image from individual images of a digital radiology system, in particular for creating a long cassette recording in stepping acquisition mode.

In digital radiography, in particular during the imaging of large areas of the body, the receive detector often limits the size of the anatomically displayable area. For example the display of the spinal cord exceeds the extent of the image receivers that are available nowadays by a multiple in some cases. For these purposes a plurality of images must be prepared in such a case in a spatial and temporal sequence and subsequently combined into a single image (referred to here as a combination image). For example in the so-called stepping method, the x-ray source and the detector are moved vertically on the x-ray stand and a number of images are recorded at different vertical positions. A further known method is the ortho tilting method, in which the center of gravity of the x-ray source itself remains in a fixed position and only the beam cone is aligned to a detector center moved vertically.

Imaging errors occur in a combination of individual recorded images, caused by the parallaxes of the beam cone of the x-ray source and the three-dimensionality of the recorded object. A single image plane perpendicular to the recording direction (referred to here as the reconstruction plane) could be shown without errors, but image elements that are present in the remaining image planes create incorrect displays in the combination image. FIG. 1, which will be explained in greater detail below, presents these problems with reference to an example.

The removal of the reconstruction plane of the object from a predetermined housing surface or a support surface (also referred to as the reconstruction plane distance) is often also referred to by the expression table-object distance, or TOD value.

United States patent application US 2011/0188726 A1 and U.S. Pat. No. 9,109,998 B2 disclose a method for obtaining a panoramic x-ray image of a Region of Interest (ROI), which is focused in a chosen Plane of Interest (POI; a plane relevant for the ROI). The method comprises the following steps:

Positioning of seam markings along the ROI;
Use of an x-ray system with an x-ray source and a detector for acquiring a number of x-ray images, which cover an ROI that is larger than the field of view of the x-ray system;
Detecting the marking elements in the separate x-ray images;
Aligning the separate x-ray images in accordance with the marking elements;
Adjusting the separate x-ray images and/or their alignment, in order to take account of the difference between the distance of the x-ray source from the surface of the marking elements and the distance from the x-ray source to the POI; and
Constructing the resulting panorama image by choosing or combining for each pixel in the resulting panorama image a value of the suitable pixels in the suitable separate x-ray images.

The seam markings are positioned so that they are not necessarily positioned within the chosen POI; but are shown in all relevant images however.

United States patent publication US 2016/0042537 A1 teaches a method for dynamic reconstruction of three-dimensional tomographic images from a set of projection images. The method includes:

Execution of programming instructions by a processing device, which are configured to cause the processing device to carry out a method that comprises the following steps:
Loading of a set of projection images into a memory device;
Specifying a reconstruction method for the set of projection images;
Reconstructing a 3D tomography image from the set of projection images that is to be displayed to a user;
Rendering and causing a screen to display the reconstructed 3D tomography image; and
Providing one or more improvements for an advanced image processing and manipulation of 3D tomography data, which is contained in the reconstructed 3D tomography image.

U.S. Pat. No. 9,858,663 B2 describes an image creation method, comprising:

Obtaining a plurality of 2D images through an object to be imaged;
Obtaining a 3D image dataset of the object to be imaged; possibly registration of the 2D images with the 3D image dataset;
Defining an image reconstruction plane in the 3D image dataset, which is the plane of an image to be reconstructed from the number of 2D images;
For a pixel in the image reconstruction plane: Mapping corresponding pixel values from the plurality of 2D images thereon and combining the imaged pixel values to a single value, in order to obtain a value for the pixel in the image reconstruction plane.

U.S. Pat. No. 7,421,057 B2 discloses an x-ray CT device, which has:

A data acquisition device for acquisition of projection data of a subject by a spiral scan, which is synchronized with a heartbeat;
An image reconstruction device for reconstruction of an image on the basis of the acquired projection data; and
A control device for controlling the data acquisition device and the image reconstruction device, wherein the control device has:
First control means for changing the spiral pitch according to a change of the heartbeat during the spiral scan;
And second control means for reconstruction of images in a number of slice positions at equal intervals on the basis of projection data, which also contain the projection data acquired during the change of the spiral pitch.

U.S. Pat. No. 7,218,766 B2 describes a method for the analysis of a plurality of views of an object, which contains an edge section extending partly from a surface of the object into an inner volume of the object, with the step of analyzing each acquired view, wherein the step of analyzing each acquired view contains the step of analyzing the edge section.

In the prior art it is usual that a TOD value determined for all individual images will be used for creating the combination image, wherein the individual images will be overlaid on one another with an overlap in accordance with this TOD value.

This is disadvantageous however, at least when the structure to be examined does not run in one reconstruction plane. A typical example of this is the double-S-shaped structure of the human spinal column, which especially in the case of a marked scoliosis, contains both relevant bone portions on the rear side of the patient, e.g. typical lumbar vertebrae: L5, with a very small distance from the detector, and also relevant bone portions, e.g. thoracic vertebrae: typically Th7-Th8, on the front side of the patient. The vertical distance between these two regions and thus the difference between the reconstruction planes for these regions can amount to several tens of centimeters in such cases. With the previous usual entry of a fixed TOD either the rear plane will be correctly displayed and there are typical compressions on the front side, e.g. double ribs, or the front side will be correctly reconstructed but spine elements on the rear side will be duplicated as a result of the geometry and thus likewise displayed distorted.

SUMMARY OF THE INVENTION

It is accordingly an object of the invention to provide a method and device which overcome the above-mentioned and other disadvantages of the heretofore-known devices and methods of this general type and which make available an improved device and also a method for fine adjustment of the reconstruction plane of a digital combination image.

With the foregoing and other objects in view there is provided, in accordance with the invention, a device for fine adjustment of a reconstruction plane of a digital combination image composed from individual images of a digital radiology system, comprising:

an interface for providing at least two individual images showing different views or regions of the same object from mutually different perspectives and each individual image having an overlapping region with at least one further individual image;

a distance controller configured to define a distance value D as a function of a controller setting of said distance controller;

a processing unit connected to said interface and said distance controller and configured to calculate a current combination image from the individual images from a current distance value D determined by said distance controller in each case in a predetermined arrangement, wherein the individual images are each shifted relative to one another by a distance A based on the current distance value D determined by said controller; and a display unit connected to said processing unit for displaying the current combination image composed from the individual images.

The inventive device for fine adjustment of the reconstruction plane of a digital combination image from individual images of a digital radiology system, e.g. an x-ray system or a tomosynthesis system, especially for creating a long cassette recording in the stepping acquisition mode, comprises a number of components, which interact functionally.

One component is an interface for providing at least two individual images. This interface can be a pure data interface, by means of which image data can be transmitted to the device, e.g. by means of a data medium or via a network. This interface can also interact in a medical device with a reconstruction unit and provide reconstructed images directly.

The individual images show different views or regions of the same object, from different perspectives, especially from different lateral positions or from different angles. These individual images can be two-dimensional or three-dimensional images, depending on their application.

An object is especially a human patient, but depending on application however, an animal or an inanimate object can also serve as an object. The object should advantageously not change its shape or its position significantly during the recording of the individual images, so that the individual images are in a sensible relationship to one another, as is already the case with current recordings of individual image combinations. With animate objects "not significantly" means that unavoidable movements, such as heartbeat or breathing for example, are tolerable, but intentional movements of extremities or of the torso on the other hand are not.

Each individual image should have an overlapping region with at least one further individual image. In such an overlapping region the same elements or part regions of the object are shown. In a recording of a number of individual images in a sequence the two outermost individual images of the sequence each have one overlapping region with their neighbors. The remaining individual images each have two overlapping, regions with their two respective neighbors.

A further component is a distance controller, which can be embodied as a real physical unit or virtually as a controller on a touch screen and can preferably take the form of a rotary control or slider control. This distance controller is embodied to determine a distance value D as a function of a controller setting, especially when it is actuated or each time that it is actuated.

A further component is a graphics processing unit, which is designed to create a current combination image in each case from a current distance value D determined in each case by the distance controller from the individual images in a predetermined arrangement, as a rule repeatedly. This arrangement is mostly the sequence of their respective recording positions, so that a meaningful overall image is produced. Two individual images are shifted in this case relative to one another by a distance A, which is based on the currently defined distance value D, wherein an individual shift for all individual images in turn is to be undertaken.

It should be noted that the values A and D are different variables, even if they can have the same value numerically. The distance value D is produced from the setting of the distance controller. The distance A is the relative distance between two individual images in the display. The two values, both A and also D are very closely linked to the distance from the reconstruction plane TOD, wherein considered purely geometrically the distance A is mostly orthogonal to the distance from the reconstruction plane TOD, at least when the images are shifted in parallel to the reconstruction plane. As a result of the nature of the parallax of the beam cone however there always exists a strict linear relationship between the distance to the reconstruction plane TOD and the numerical values A or D, so that for example the value D set at the distance controller can be seen as a measure for TOD, even if the numerical values do not match exactly. More precisely TOD is produced by the formula:

$$TOD = TOD_0 + x \cdot W \tag{i}$$

wherein $TOD_0$ is a constant, which in a simple case has the value 0, x is a constant value not equal to 0 and W is either A or D. The numerical value of $TOD_0$ and x depends on whether D or A was selected for W. The distance of the reconstruction plane TOD is always positive as a rule, since it involves an observable variable. The same also applies especially for the values $TOD_0$ and x. If TOD assumes the value $TOD_0$, this mostly means in practice that the reconstruction plane coincides with the surface of an examination table or the housing wall or an ortho stand for patients.

A further component is a display unit for displaying the current combination image from the individual images, e.g. a screen, which in particular can also be embodied as a touch screen for displaying the distance controller.

An inventive image evaluation system or x-ray system comprises an inventive device as has been described above, and its preferred forms of embodiment will be explained in more detail below. An image evaluation system can be a diagnostic station for example, but can also be a terminal computer at which a physician interpreting the findings undertakes their checking of the images.

With the above and other objects in view there is also provided, in accordance with the invention, a method for fine adjustment of the reconstruction plane of a digital combination image from individual images of a digital radiology system, e.g. of an x-ray system, especially with a device as outline above. The novel method comprises the steps:

provision of at least two individual images, wherein the individual images show different views or regions of the same object from different perspectives, and wherein each individual image has an overlapping region with at least one further individual image, display of a first combination image from the individual images in a predetermined arrangement on a display unit of a processing unit, definition of a distance value D as a function of a controller setting of a distance controller, calculation of a current combination image from the individual images in a predetermined arrangement, from a current distance value D determined by the distance controller in each case, wherein the individual images are each shifted relatively in relation to one another by a distance A, which is based on the currently determined distance value D, display of the current combination image.

It should be noted that the shifting can relate to all individual images, wherein it is preferred in practice for just two individual images or individual image groups to be shifted relative to one another and for the process to be carried out for changing individual images or individual image groups until such time as an optimum combination image has been produced. In a linear series of individual images it is worthwhile for example retaining an edge image and shifting the neighbors of this edge image until such time as the optimum TOD value in relation to these two images has been reached. Then the procedure is exactly the same for the next neighboring individual image of the image group set, and so forth, until an optimum TOD value has been set in each case for all individual images in succession.

The invention is thus especially in a position to combine individual images, which have been recorded by means of a digital radiology system, e.g. with ortho accessory available, in a stepping method, in particular with the assistance of the parameters present in the system, e.g. source to image distance (SID), pixel size of the image receiver, geometrical detector position as a function of the respective recorded image and also the incorporation, combine them into a long image (combination image) and to carry out the individual entry necessary for this of the desired reconstruction plane (TOD value), by the distance controller as a dynamic user interface element.

Please note that by means of a distance controller each overlapping region between two individual images, i.e. the respective distance A between two individual images, can be set individually for all neighboring individual image pairs, which means that the reconstruction plane can vary at each image edge. In this way it is possible, in individual images, to follow the course of an extended structure e.g. the spinal column, in space and always to adapt the reconstruction planes at the seams of the individual images to the desired object. This is especially sensible for particularly unfavorable anatomies.

A large part of the previously mentioned components of the system can be realized entirely or in part in the form of software modules in a processor of a corresponding control or processing device. A largely software-based realization has the advantage, that infrastructure already used previously can be upgraded in a simple manner by a software update in order to work in the inventive manner. To this extent the object is also achieved by a corresponding computer program product with a computer program, which is able to be loaded directly into a memory device of an image evaluation system and/or of an x-ray system, with program sections for carrying out all steps of the inventive method when the program is executed in the control device. Such a computer program product, as well as the computer program, can if necessary comprise additional elements such as e.g. documentation or additional components, including hardware components, such as e.g. hardware keys (dongles etc.) for use of the software.

Also preferred is a computer-readable storage medium, on which program sections able to be read in and executed by a processing unit are stored, in order to carry out all steps of the inventive method when the program sections are executed by the processing unit.

Further especially advantageous embodiments and developments of the invention emerge from the dependent claims and also from the description below. In this case the features for forms of embodiment of one category can also serve to characterize forms of embodiment of another category. For example the inventive device can also be developed analogously to the dependent method claims or parts of the description, wherein the same also applies conversely for the method claims. In particular individual features of various exemplary embodiments or variants can also be combined to form new exemplary embodiments or variants.

Preferably the distance value D is a measure for the position of a reconstruction plane perpendicular to the direction of recording of the individual image, which means in particular that x from the formula (i) given above has the value 1, and in particular $TOD_0$ additionally has the value 0, which would mean that D would be numerically identical to TOD. The relative distance A of the individual images concerned is preferably calculated in this case starting from an initial, constant distance $A_0$ and a constant value b in accordance with the formula:

$$A = A_0 - b \cdot D \tag{ii}$$

In accordance with an added feature of the invention, the device has at least one additional controller, which is embodied (when actuated) to determine as a function of its controller setting a further position value, e.g. lateral position or orientation in space. This position value thus specifies a measure for the tilting of the image plane of an individual image or for a shift of an individual image parallel to its image plane.

This additional controller is particularly advantageous for the use of three-dimensional individual images or volume-individual images, e.g. in tomosynthesis. For example it can be necessary in the three-dimensional case for not only the distance between two individual images to have to be shifted, but also for a tilting of the individual images in relation to each other to be necessary. Moreover it can occur that—in particular with volume-individual images—a lateral shift, e.g. perpendicular to the distance of the individual images described above, must be undertaken.

Preferably the distance controller or the additional controller are assigned a fixed maximum and minimum value of the distance value D or of the value for the tilting/shift. The maxima and minima of the respective value in this case are in particular set permanently in the system or they are calculated, wherein other minimum/maximum values are included if necessary in each case for different scenarios. This has the advantage that the values able to be set by a controller always move within a meaningful range. Advantageously the maximum or minimum values are always governed by the medical circumstances. Thus the distance value D can preferably be set by means of the distance controller between a minimum distance value $D_{min}$ and a maximum distance value $D_{max}$, which corresponds to a sensible TOD value. The maximum distance value $D_{max}$ in this case preferably corresponds to a TOD value, which corresponds to a position of a reconstruction plane within the object, but above the structure to be examined. The minimum distance value $D_{min}$ is preferably ≥0 and in particular likewise corresponds to a TOD value, which corresponds to a position of a reconstruction plane within the object, but below the structure to be examined. The direction specifications naturally relate to the orientation to the x-ray source, wherein "above" is the side facing towards this x-ray source.

Preferably the processing unit is embodied so that a definition of a new, current distance value D or further position value applies to a whole group of individual images, of which the relative positions or orientations to one another remain constant. This enables an image group already set to be fixed. In particular, when the distance controller is actuated, the relative distances between individual images of the group of individual images, i.e. between at least two individual images, remain the same in relation to one another, while this group is shifted relative to at least one further individual image based on the distance value D. To this extent the image group can also be seen as a combination image (already created in a previous step), which in a current step is one of the individual images to be combined or a corresponding group of individual images. Likewise the two current individual images or an image group to be combined can be combination images already created previously.

Preferably the processing unit is designed such that, in each part of the overlapping region of two individual images in a combination image, only the image information of one of the overlapping individual images in each case is accepted. A part of the overlapping region can be formed in this case from the image information of the one individual image and a part from the image information of the other. As a simple option it is preferred that the overlapping region relating to the acceptance of the image information is divided in half, i.e. the half of the overlapping region of each image is cut off at the corresponding image edge. A preferred more complex solution initially searches for relevant structures on the respective individual images and cuts out that image information that shows the structures less accurately.

As an alternative it is preferred that the processing unit is designed, so that with the overlapping of two individual images in the combination image, the transparency of the image information of at least a first of the individual images, especially preferably of both individual images, is enlarged, preferably constantly, in the overlapping region in the direction towards the respective other (second) individual image. In particular the transparency at the corresponding edge of the first and possibly also the second image concerned lying at the end of the overlapping region (U) amounts to 100%. This has the advantage that the images flow seamlessly into one another. This alternative is possibly able to be combined advantageously with the previously described option of cutting out information, especially as part of the solution in which structures are sought. Here irrelevant image regions, in which no relevant structures are contained, can simply be cut out and image regions with relevant structures can merge into one another by changing the transparency.

Preferably the device additionally comprises a virtual or real selection unit, e.g. a switch or button, the actuation of which brings about a storage of a value set by the distance controller and/or the additional controller. The distance value D or the value for the tilting or shifting and thus the relative position of two individual images can be fixed with this selection unit. In particular through an operation of the selection unit the functionality of the distance controller and/or of the additional controller can be separated from the individual images concerned and preferably allocated to a further individual image. The shifted individual images will thus be decoupled from the controller and can initially no longer be shifted until they are allocated to this controller again. By the automatic allocation of the function of the distance controller or additional controller to a further individual image theoretically a distance controller and a selection unit are sufficient to combine a series of individual images successively into a combination image with optimally set reconstruction planes. In particular fixed individual images, after actuation of the selection unit, form a group of individual images or a combination image serving for further use as a new individual image, as has already been described above.

Preferably the distance controller is allocated a predetermined start value (default value), which corresponds to a calculated or predetermined typical distance value $D_{typ}$. The designation "typical" relates in such cases to a usual value for a specific recording scenario, and depends on the examination object, the task and the established position of the object or corresponding circumstances. To this end the distance controller will preferably be preset initially to a value established in the organ program setup. This has the advantage that the medical staff conducting the examination are saved further time in the diagnosis of simply structured anatomies.

Preferably the processing unit is designed so that the combination of the individual images into a combination image and its display preferably occurs in real time, i.e. not later than 0.5 seconds, in particular not later than 0.1 seconds, after actuation of a controller. This has the advantage that it is made possible for the user in the event of a largely constant reconstruction plane, e.g. the leg bones, to have a flowing and thus convenient entry of this central parameter and in particular in the case of a dynamic reconstruction plane, e.g. double-S spinal column, with strong lateral shift caused by scoliosis, an "in-situ journey" through all relevant planes is made possible.

In accordance with a further feature of the invention, the individual images are recorded by way of one of the following processes:

the x-ray source and the image receiver of the digital radiology system are shifted laterally, parallel to the reconstruction plane, or the x-ray source is tilted and the image receiver is shifted laterally, parallel to the reconstruction plane, whereby the individual images represent regions of the object from different laterally shifted recording positions each with parallel recording planes or from different recording directions, or the x-ray source and the image receiver are tilted and present the object from different recording angles, wherein the x-ray source and/or the image receiver are preferably also shifted in addition, in particular on an arcuate, or circular path, which is advantageous for a tomosynthesis for example.

An advantage of the invention is that, depending on the diagnostic problem involved, a number of reconstruction planes could be needed, and the invention guarantees this.

A further advantage of the invention is that a good overview of the anatomical situation is always guaranteed, which is associated with added value in the diagnosis and with a reduction in the risk of incorrect inputs relevant to the diagnosis.

Other features which are considered as characteristic for the invention are set forth in the appended claims.

Although the invention is illustrated and described herein as embodied in a device and method for fine adjustment of the reconstruction plane of a digital combination image, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
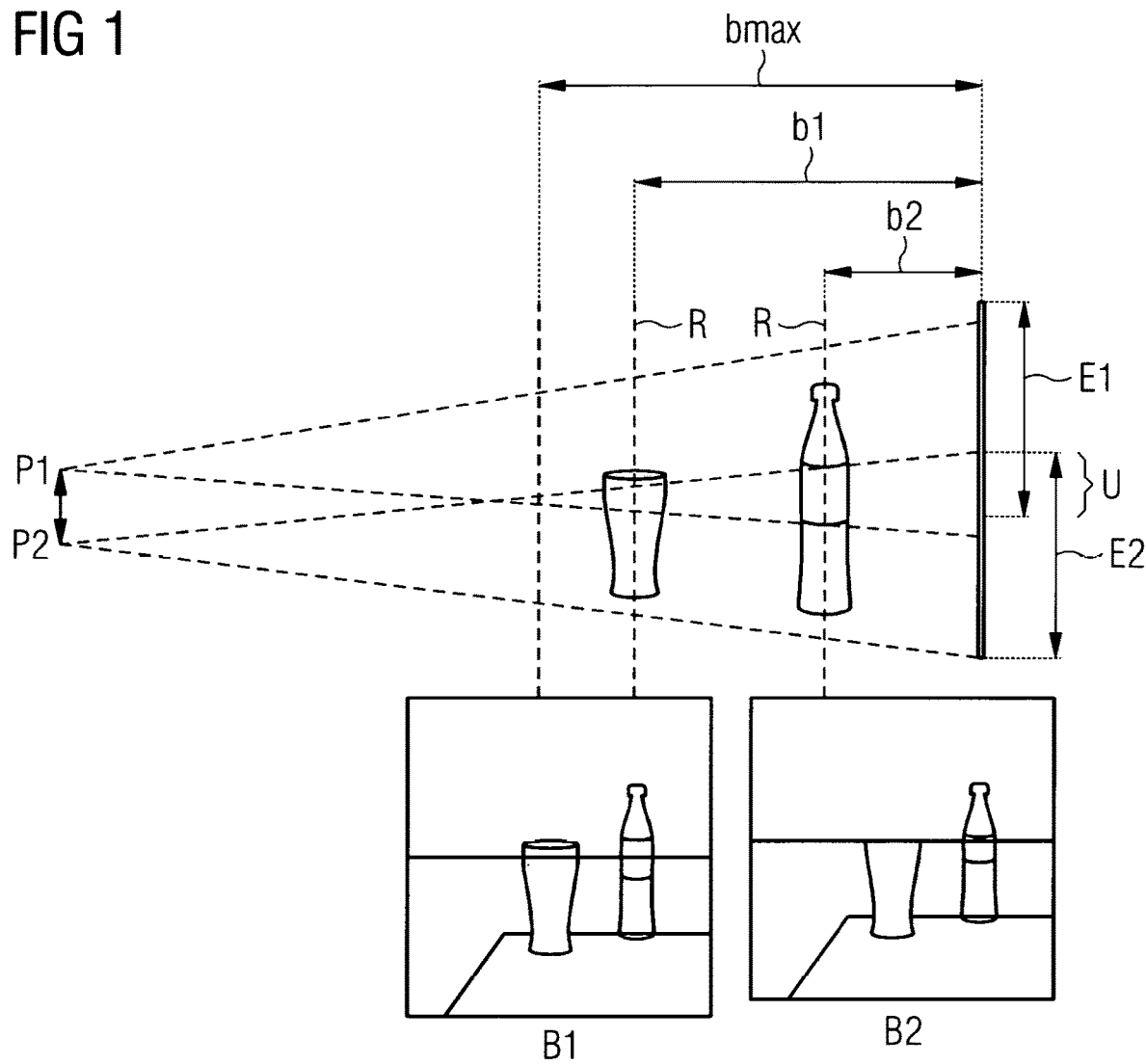
FIG. 1 is an illustration of the underlying problems addressed by the invention.

Referring now to the figures of the drawing in detail and first, particularly, to FIG. 1 thereof, there is shown an illustration of the underlying problems addressed by the invention. Two objects, a glass and a bottle, which are to be viewed as representative of structures in an object (e.g., in a patient), are located in different positions b1 and b2, at a distance in relation in each case to reconstruction planes R each running through the central point of these objects from two illumination points P1, P2. These points P1 and P2 can be seen as recording points, however the invention resides in the field of x-ray imaging, which a fluoroscopy shows better for better visualization. With a medical recording the B values would correspond to the TOD values. The dashed lines indicated in the drawings at distances b1, b2 and bmax correspond to potential reconstruction planes R.

A first individual image E1, which is illuminated from point P1, shows a part of bottle and glass, a second individual image E2, which is illuminated from P2, shows another part of bottle and glass, wherein, as can be seen in the diagram, an overlapping region U exists, in which in each case the same parts of bottle and glass are recorded, but which are shifted perspectively because of parallaxes.

If the two individual images are laid on each other overlapping so that the glass is shown correctly, as is to be seen in the left-hand image B1 (reconstruction plane R at distance b1), the bottle is not shown correctly, because it appears that parts of the label are duplicated. If on the other hand the two individual images are laid overlapping on one another so that the bottle is shown correctly, as is to be seen in the right-hand image B2 (reconstruction plane R at distance b2), the glass is not shown correctly because a part appears to be missing.

In the case in which the bottle would be the structure of interest, the distance b2 of the individual images would have to be selected so that the situation of the plane at distance b2 is shown well, which corresponds to the lower right-hand image B2. In the case in which the glass would be the structure of interest, the distance b1 of the individual images would have to be selected so that the situation of the plane at distance b1 is shown well. The distance of the individual images has a logical linear link to the reconstruction plane.

Figure 2:
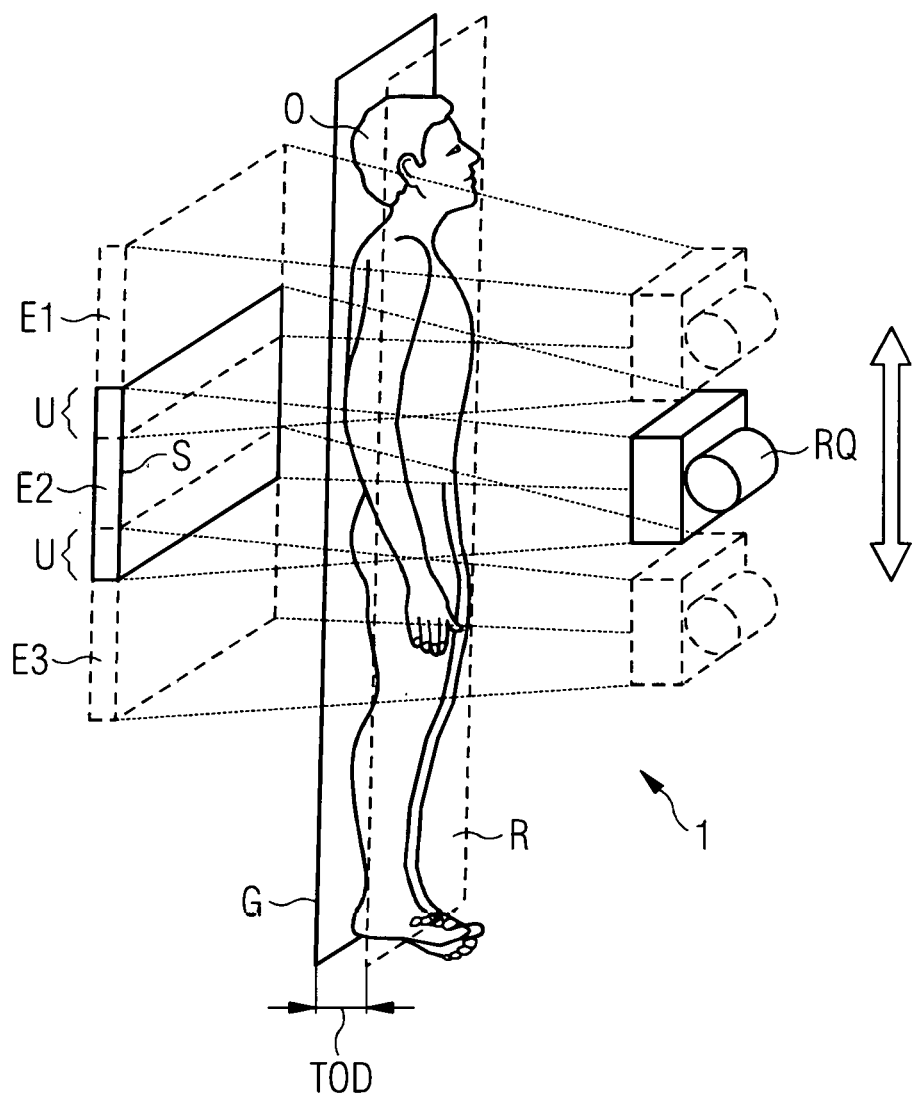
FIG. 2 shows a schematic diagram of a preferred recording of individual images.

FIG. 2 shows perspectively a schematic diagram of a preferred recording of individual images with an x-ray system 1, which is representative here of a digital radiology system 1. An x-ray source RQ radiates x-rays through a person O, who represents the object O here, and stands in front of a housing wall G permeable to x-rays. Shown in the drawing in parallel to the housing wall G is a possible reconstruction plane R with a distance TOD. After the irradiation the x-rays, of which the ray path is shown by dashed lines, are registered by an image sensor S and an individual image E2 is created from the information of the image sensor S.

The x-ray source RQ and the image sensor S are shifted in the direction of the double-ended arrow and further individual images E1, E3 are recorded (shown by dashed outlines). In such cases it is insured that neighboring individual images E1, E2, E3 each have an overlapping region U, in which duplicated image information is present, but of course perspectively distorted by the parallaxes.

Figure 3:
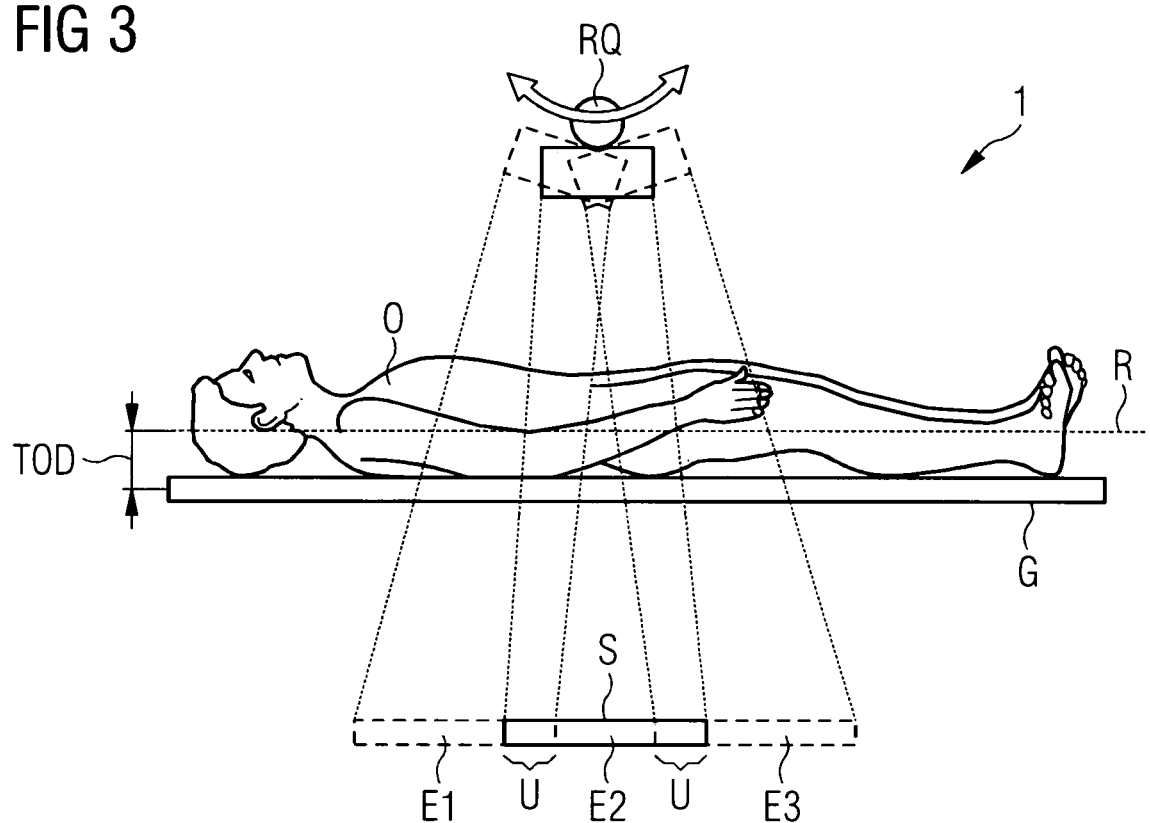
FIG. 3 shows a schematic diagram of a further preferred recording of individual images.

FIG. 3 shows in a side view a schematic diagram of a further preferred recording of individual images with an x-ray system 1. The recording of the individual images E1, E2, E3 with the respective overlapping regions U proceeds in a similar manner to that shown in FIG. 1, with the sole difference that the x-ray source is not shifted but is tilted.

The person O is not standing here, but is lying on an examination table G. Shown in the figure in parallel to this examination table G is a possible reconstruction plane R with the distance TOD.

Naturally instead of three individual images, just two or any given number more can be recorded. There is also no absolute stipulation as to a common direction of recording. Theoretically two or more series can also be recorded alongside one another.

In practice, depending on the choice made by the operator, a step width for a perpendicular movement of the x-ray source RQ and of the image sensor S and from this in its turn a local position of the overall detector can be selected as a function of the individual image in each case, e.g. in order of the recordings from top to bottom. This information is also referred to as "DET POS" and is transferred to the central unit of the system controller, as is the specification of the field of vision ("COL"). From this, the central unit can calculate in advance, possibly with the assistance of further fixed values known to the system such as e.g. the distance from the source to the plane of the image sensor S ("SID") and the pixel size of the detector ("DET SIZE"), the point at which the single individual images must be combined in the image system, but also which is the maximum sensible TOD for the reconstruction, so that all portions of the image can be safely mapped. Moreover a sensible typical TOD (or a sensible value for the distance controller $D_{typ}$) can also be established from a database for organ data and likewise transferred to the image system. On the image system this data is used for a two-dimensional combination in this case, which can be assessed in-situ, as the following description of FIG. 4 shows.

Figure 4:
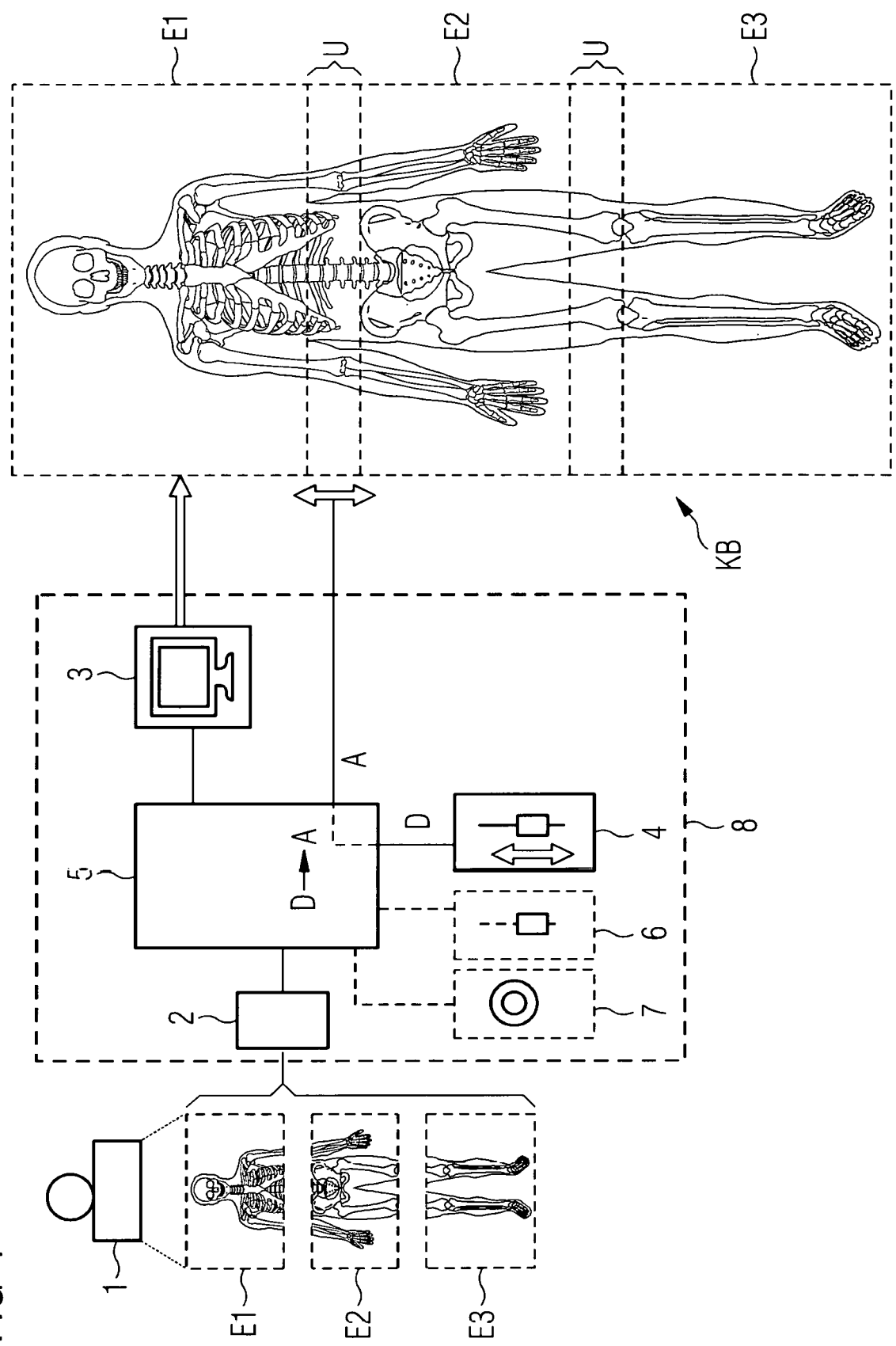
FIG. 4 shows a schematic diagram of a preferred form of embodiment of an inventive system and of the way in which it functions.

FIG. 4 shows a schematic diagram of a preferred form of embodiment of an inventive device (8) and the way in which it functions within the framework of a block diagram. Three individual images E1, E2, E3 with overlapping regions U are recorded by an x-ray system 1 (only the symbol of the x-ray source is indicated here as representative), e.g. as described above, and provided via the interface 2 to the device. as indicated graphically, the individual images E1, E2, E3 show different parts of the person O.

Via the interface 2 the individual images E1, E2, E3 are accessible to the graphics processing unit 5 and can be presented as combination image KB with overlapping individual images E1, E2, E3. The size of the respective overlapping regions U in this case is able to be set by means of a distance controller 4. Here the distance controller 4, which can be present as a physical unit, but can also be present as a slider on a display device with touch screen, is functionally logically linked to the upper two individual images. If the slider of the distance controller 4 is moved up and down in the direction of the double-ended arrow on the distance controller 4 a changing distance value D will be transferred to the processing unit 5. Said unit allocates the numerical value of D to a distance A, which defines the distance of the upper two individual images E1, E2. With an actuation of the distance controller 4 the upper two individual images E1, E2 thus shift in the direction of the double-ended arrow there and the upper overlapping region changes.

For example the TOD is set as D directly on the distance controller 4 and can in particular also be read from said controller. It makes sense for the distance controller 4 to be able to define the value D from a minimum TOD, e.g. 0, up to a maximum TOD, wherein all distances belong to reconstruction planes, which lie in the body of the person O. A movement of the distance controller 4 thus enables the user to move through all geometrically sensible reconstruction results, and in this case retains an overview of the anatomical situation.

The combination image is shown on the display unit 3 for the user. For an optimum setting of the overlapping region U of the individual images E1, E2, E3 and thus also automatically of the respective reconstruction planes R, it is of advantage for the respective current combination image KB to be shown in real time, i.e. for not more than 0.5 seconds, in particular not more than 0.1 seconds, to elapse between actuation of the distance controller 4 and the display of the corresponding combination image KB.

Optionally a further controller 6 can be present, by means of which other changes can be made to the individual image positions.

As a further option a selection unit 7 can be present, by means of which the positions of individual images E1, E2, E3 can be fixed. For example an actuation of this selection unit 7 could fix the distance of the upper two individual images E1, E2, separate the functionality of the distance controller 4 and now allocate it to the lower individual image E3. It would thus be possible to align the upper two individual images E1, E2 optimally with one another and, at the touch of a button, to switch to the alignment of the lower individual image E3. A further actuation could fix the entire combination image KB.

In conclusion it is pointed out once again that the method previously described in detail above and also the device presented merely involve exemplary embodiments, which can be modified by the person skilled in the art in a very wide diversity of ways, without departing from the area of the invention. Furthermore the use of the indefinite article "a" or "an" does not exclude the features concerned also being able to be present more than once. Likewise the term "unit" and "module" does not exclude the components concerned consisting of a number of interacting subcomponents, which if necessary can also be physically distributed.

The following is a summary list of reference numerals and the corresponding structure used in the above description of the invention:

1 X-ray system/digital radiology system
2 Interface
3 Display unit
4 Distance controller
5 Processing unit
6 Additional controller
7 Selection unit
8 Device
A Distance
D Distance value
G Housing surface/examination table
B1, B2 Image
b1, b2 Distance/position
E1, E2, E3 Individual image
KB Combination image
O Object/person
R Reconstruction plane
RQ X-ray source
S Image receiver
TOD Distance of the reconstruction plane
U Overlapping region

The invention claimed is:

1. A device for fine adjustment of a reconstruction plane of a digital combination image composed from individual images of a digital radiology system, comprising:
  an interface for providing at least two individual images showing different views or regions of the same object from mutually different perspectives and each individual image having an overlapping region with at least one further individual image;
  a distance controller configured to define a distance value D as a function of a controller setting of said distance controller;

a processing unit connected to said interface and said distance controller and configured to calculate a current combination image from the at least two individual images from a distance value D determined by said distance controller in each case in a predetermined arrangement, wherein the at least two individual images are each shifted relative to one another by a distance A based on the distance value D determined by said distance controller; and a display unit connected to said processing unit for displaying the current combination image composed from the at least individual images.

2. The device according to claim 1, wherein the distance value D is a measure for a position of a reconstruction plane perpendicular to a direction of recording of each individual image, and wherein a relative distance A of the individual images concerned is calculated in accordance with $$A = A_0 - b \cdot D,$$

wherein $A_0$ is an initial distance and b is a constant value.

3. The device according to claim 1, further comprising at least one additional controller configured to determine a further position value as a function of a controller setting of said additional controller, the further position value being a measure for a tilting of an image plane of an individual image or for a shifting of an individual image in parallel to its image plane.

4. The device according to claim 3, wherein at least one of said distance controller or said additional controller are assigned a fixed maximum and/or a fixed minimum value.

5. The device according to claim 1, wherein said processing unit is configured such that a definition of a new distance value and/or a further position value applies for a group of individual images, of which the relative positions or orientations to one another remain constant.

6. The device according to claim 1, wherein said processing unit is configured such that in each part of the overlapping region of two individual images in the combination image only image information of one of the at least two individual images is transferred.

7. The device according to claim 6, wherein said processing unit is configured to divided the overlapping region in half in relation to a transfer of the image information.

8. The device according to claim 1, wherein said processing unit is configured such that, in an overlap of two individual images in the combination image a transparency of the image information of a first individual image in an overlapping region is increased in a direction of a second individual image.

9. The device according to claim 8, wherein said processing unit is configured to increase the transparency to a maximum of 100% at an edge of the first individual image lying in the area of the second individual image at the end of the overlapping region.

10. The device according to claim 1, further comprising a selection unit which, upon being actuated, causes a value set by the distance controller and/or an additional controller to be stored.

11. The device according to claim 10, wherein said selection unit then separates a functionality of the distance controller and/or of the additional controller from the individual images.

12. The device according to claim 1, wherein said distance controller is allocated a predetermined start value, which corresponds to a calculated or predetermined distance value.

13. The device according to claim 1, wherein said processing unit is configured to combine the at least two individual images and to display the combination image in real time.

14. An image evaluation system and/or digital radiology system, comprising a device according to claim 1.

15. A method for fine adjustment of the reconstruction plane of a digital combination image from individual images of a digital radiology system, the method comprising the steps:

providing at least two individual images, the at least two individual images showing different views or regions of the same object from different perspectives, and each individual image having an overlapping region with at least one further individual image;

displaying a first combination image from the at least two individual images in a predetermined arrangement on a display unit of a processing unit;

defining a distance value D as a function of a controller setting of a distance controller;

calculating a current combination image from the at least two individual images in a predetermined arrangement, from a distance value D determined by the distance controller in each case, wherein the at least two individual images are shifted relative to one another in each case by a distance A, which is based on the currently defined distance value D; and displaying the current combination image.

16. The method according to claim 15, which comprises recording the individual images by:

laterally shifting an x-ray source and an image receiver of the digital radiology system, in parallel to a reconstruction plane;

or tilting the x-ray source and laterally shifting the image receiver, in parallel to the reconstruction plane;

or tilting the x-ray source and the image receiver and representing the object from different recording angles.

17. The method according to claim 15, which comprises recording the at least two individual images by tilting the x-ray source and the image receiver and representing the object from different recording angles, and in addition shifting the x-ray source and/or the image receiver along an arcuate path.

18. A computer program product with a computer program, to be loaded directly into a memory device of a medical imaging system, the computer program containing program sections for carrying out all steps of the method according to claim 15 when the program is executed in the processing unit.

19. A computer-readable medium, comprising program sections to be read in and executed by a processing unit stored in non-transitory form, for carrying out all steps of the method according to claim 15, when the program sections are executed by the processing unit.

* * * * *